(12) United States Patent
Porter

(10) Patent No.: US 10,716,417 B2
(45) Date of Patent: Jul. 21, 2020

(54) THERAPEUTIC PILLOW SHAM

(71) Applicant: Selena Porter, Las Vegas, NV (US)

(72) Inventor: Selena Porter, Las Vegas, NV (US)

( * ) Notice: Subject to any disclaimer, the term of this patent is extended or adjusted under 35 U.S.C. 154(b) by 146 days.

(21) Appl. No.: 16/100,156

(22) Filed: Aug. 9, 2018

(65) Prior Publication Data

US 2019/0045952 A1 Feb. 14, 2019

Related U.S. Application Data

(63) Continuation-in-part of application No. 29/626,882, filed on Nov. 21, 2017, now Pat. No. Des. 853,752.

(60) Provisional application No. 62/543,125, filed on Aug. 9, 2017.

(51) Int. Cl.
*A47G 9/02* (2006.01)
*A47G 9/04* (2006.01)
*A47G 9/10* (2006.01)
*A47C 7/38* (2006.01)

(52) U.S. Cl.
CPC ............. *A47G 9/0253* (2013.01); *A47G 9/04* (2013.01); *A47C 7/383* (2013.01); *A47G 9/10* (2013.01)

(58) Field of Classification Search
CPC .......... A47G 9/0253; A47G 9/04; A47G 9/10; A47G 9/1036; A47C 7/383; A47C 7/38
USPC .............................. 5/490, 491, 639, 640, 636
See application file for complete search history.

(56) References Cited

U.S. PATENT DOCUMENTS

| | | | | |
|---|---|---|---|---|
| 3,538,508 A * | 11/1970 | Young | ................ | A47G 9/1045 2/414 |
| 4,763,369 A * | 8/1988 | Spector | ................ | A47G 9/1045 446/369 |
| 4,783,866 A * | 11/1988 | Simmons | ............. | A47G 9/1036 5/421 |
| 4,858,259 A * | 8/1989 | Simmons | ............. | A47G 9/1036 5/644 |
| 5,070,558 A * | 12/1991 | Fenley | ..................... | A47G 9/10 5/490 |
| 5,163,194 A * | 11/1992 | Dixon | .................. | A47G 9/1081 5/636 |
| 5,168,590 A * | 12/1992 | O'Sullivan | .......... | A47G 9/0253 5/421 |
| 5,344,437 A * | 9/1994 | Pistay | ...................... | A61F 7/10 5/639 |
| 5,367,731 A * | 11/1994 | O'Sullivan | .......... | A47G 9/0253 5/645 |
| 5,916,088 A * | 6/1999 | Gueli | ....................... | A61F 7/10 5/639 |
| 6,973,691 B1 * | 12/2005 | Cordova | ................ | A47C 7/383 248/118 |
| 9,138,086 B1 * | 9/2015 | Bamberg | ................. | A47G 9/10 |
| D853,752 S * | 7/2019 | Porter | ........................... | D6/601 |

(Continued)

*Primary Examiner* — Robert G Santos

(57) ABSTRACT

A therapeutic pillow sham that allows a user to cover any body part such as, but not limited to, the eyes, neck, chest or back of the user. The therapeutic pillow sham includes a pillowcase, a first sash, and a second sash. The pillowcase is a pillow enclosure that is able to receive a pillow. The first sash and the second sash allow the user to cover any body part. In more detail, the first sash and the second sash can be used to cover the eyes of the user in order to block out light while the user is asleep and laying on the therapeutic pillow sham. Additionally, the first sash and the second sash can receive a therapeutic insert to provide therapeutic support to any body part.

11 Claims, 10 Drawing Sheets

(56) References Cited

U.S. PATENT DOCUMENTS

| | | | | |
|---|---|---|---|---|
| 10,335,318 B2 * | 7/2019 | Bamberg | ............. | A47G 9/0253 |
| 2005/0273935 A1 * | 12/2005 | Cordova | ................ | A47C 7/383 |
| | | | | 5/652 |
| 2008/0216244 A1 * | 9/2008 | Minton | .................... | A47G 9/10 |
| | | | | 5/640 |
| 2013/0312192 A1 * | 11/2013 | Lee | ........................ | A47G 9/007 |
| | | | | 5/639 |
| 2016/0000607 A1 * | 1/2016 | Bamberg | ............. | A47G 9/1045 |
| | | | | 2/15 |
| 2019/0045952 A1 * | 2/2019 | Porter | ........................ | A61F 9/04 |

* cited by examiner

THERAPEUTIC PILLOW SHAM

The current application is a continuation-in-part (CIP) application of the U.S. design application Ser. No. 29/626,882 filed on Nov. 21, 2017 (now U.S. Design Pat. No. D853,752).

The current application claims a priority to the U.S. Provisional Patent application Ser. No. 62/543,125 filed on Aug. 9, 2017.

FIELD OF THE INVENTION

The present invention relates generally to pillows. More particularly, the present invention is a therapeutic pillow sham that includes sash portions for covering the face, eyes, nose, ears and also neck, shoulders or chest of the user. The sash portions include cavities allowing the user to introduce heating or cooling pack to the pillow sham. The pillow sham includes a loop allowing the user to display a bow shape with the sash portions being inserted into the loop.

BACKGROUND OF THE INVENTION

Pillow cases and shams are very common items used to cover pillows for decoration and/or for more comfort. The pillow cases and shams include different designs, shapes, and sizes. However, current pillow cases and shams are only meant for covering a pillow. When attempting to sleep or to rest, a person may be interrupted by sunlight or other light. There are methods to prevent this and the most common method is to use a sleeping mask. However, this method may be uncomfortable for the user. Additionally, an individual may want to cover other parts such as his or her arms, neck, ears, or other body parts. Covering other parts are not meant to block out light, but rather to block out any breeze coming from a window or air condition unit. Furthermore, current pillow cases or shams do not offer an option to introduce a heating or cooling pack to sooth body parts of an individual.

It is therefore an objective of the present invention to provide a pillow sham that includes sash portions for covering the face, eyes, nose, ears, or other parts of the user. The sash portions include cavities allowing the user to introduce heating or cooling pack to the pillow sham. The pillow sham includes loops allowing the user to display a bow shape with the sash portions being inserted into the loops. The sash portions may include additional soothers such as fur or pom-pom pieces as optional pacifiers to help the user fall asleep.

DETAIL DESCRIPTIONS OF THE INVENTION

All illustrations of the drawings are for the purpose of describing selected versions of the present invention and are not intended to limit the scope of the present invention.

Figure 1:
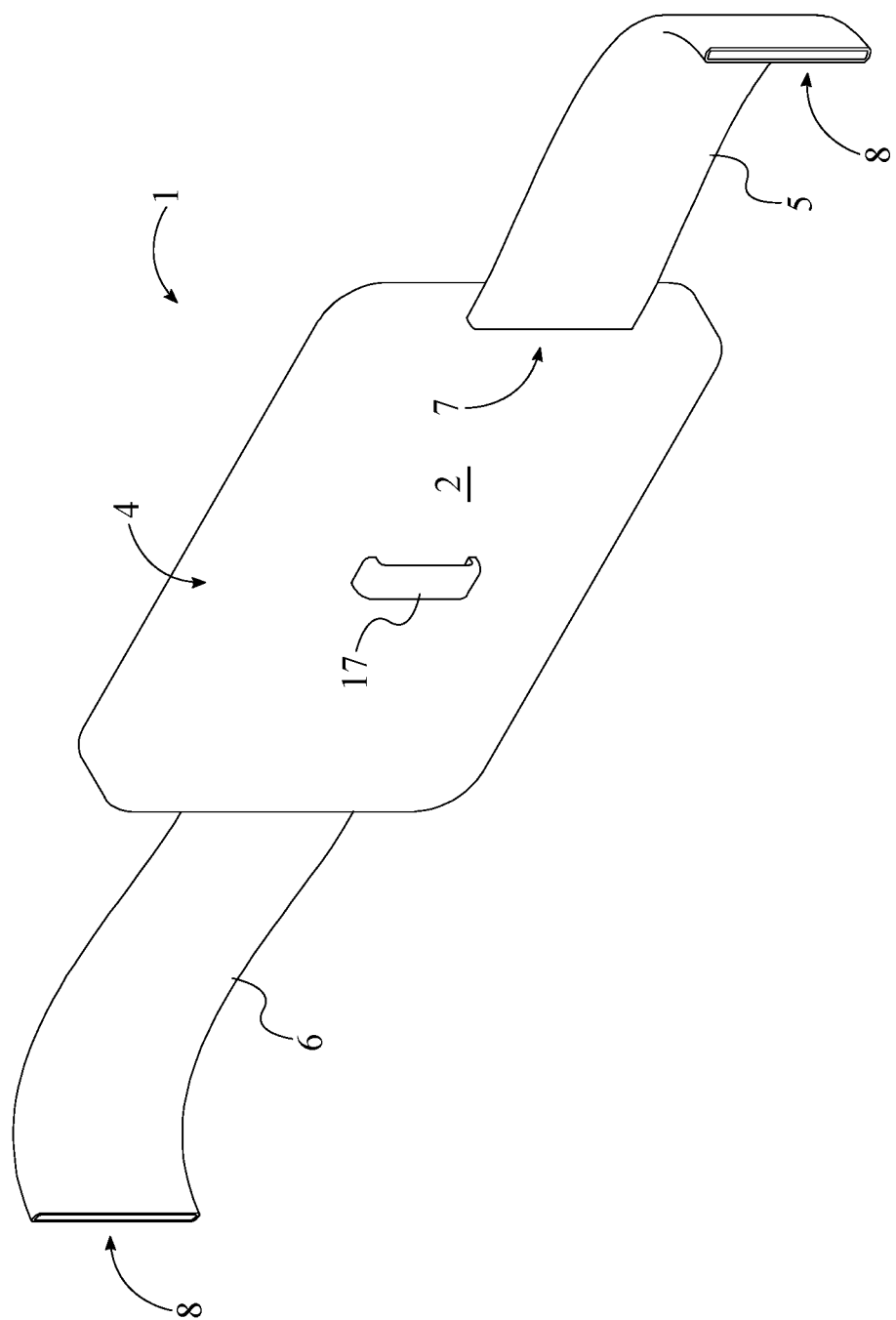
FIG. 1 is a front perspective view of the present invention.

The present invention is a therapeutic pillow sham that is used to cover body parts such as, but not limited to, the eyes, neck, chest, or back of the user. With reference to FIG. 1, the present invention includes a pillowcase 1, a first sash 5, and a second sash 6. The pillowcase 1 is a pillow cover that allows the present invention to receive any pillow. The pillowcase 1 may be any type of pillow cover such as, but not limited to, an envelope or standard pillow enclosure. The pillowcase 1 preferably includes a pillow sham design. The first sash 5 and the second sash 6 are used to cover body parts of the user such as, but not limited to, the eyes, neck, chest or back of the user. In more detail, the first sash 5 and the second sash 6 may be used to cover the eyes of the user to block out light.

Figure 2:
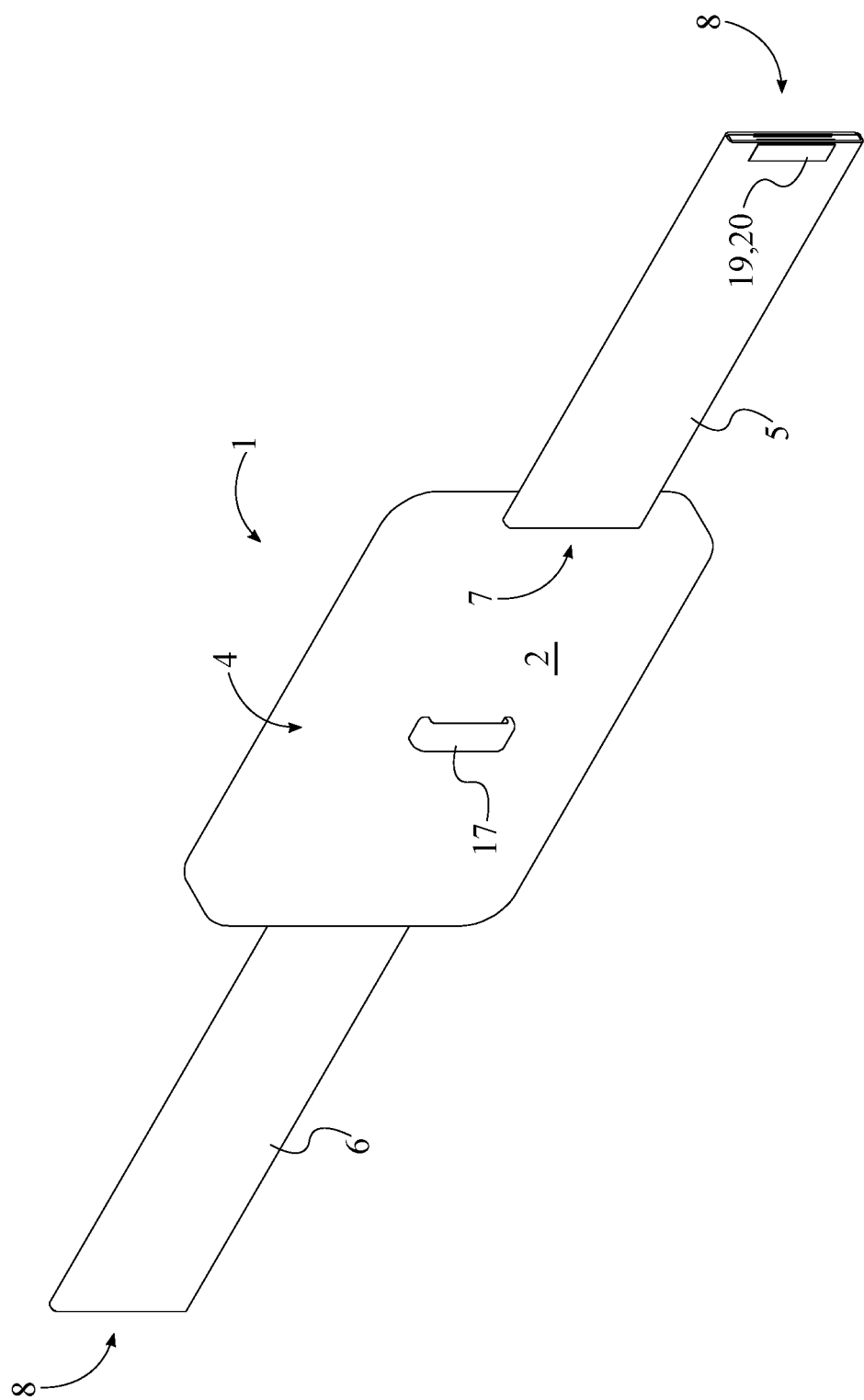
FIG. 2 is a front perspective view of the present invention displaying the sash fastener.
Figure 3:
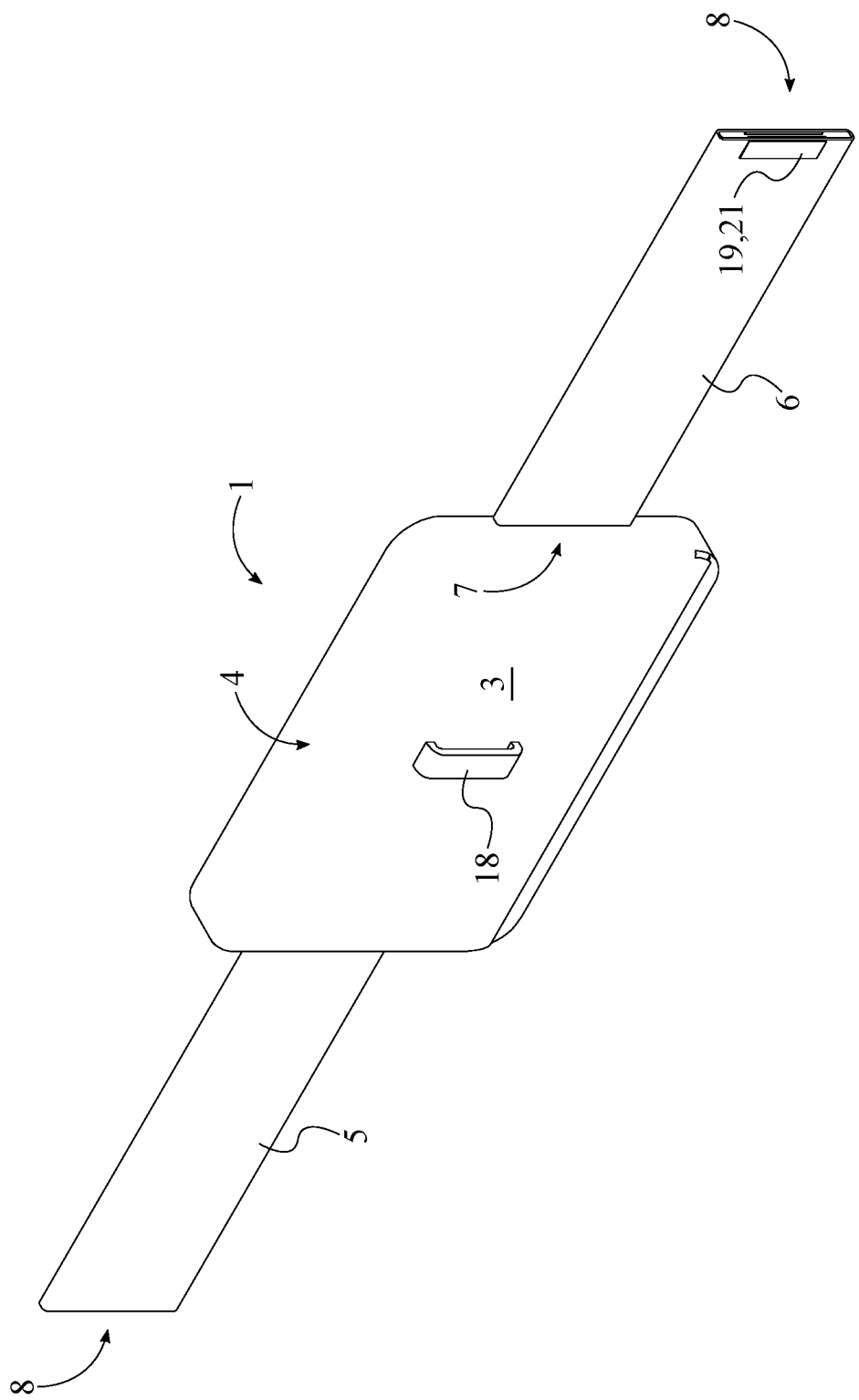
FIG. 3 is a rear perspective view of the present invention displaying the sash fastener.
Figure 4:
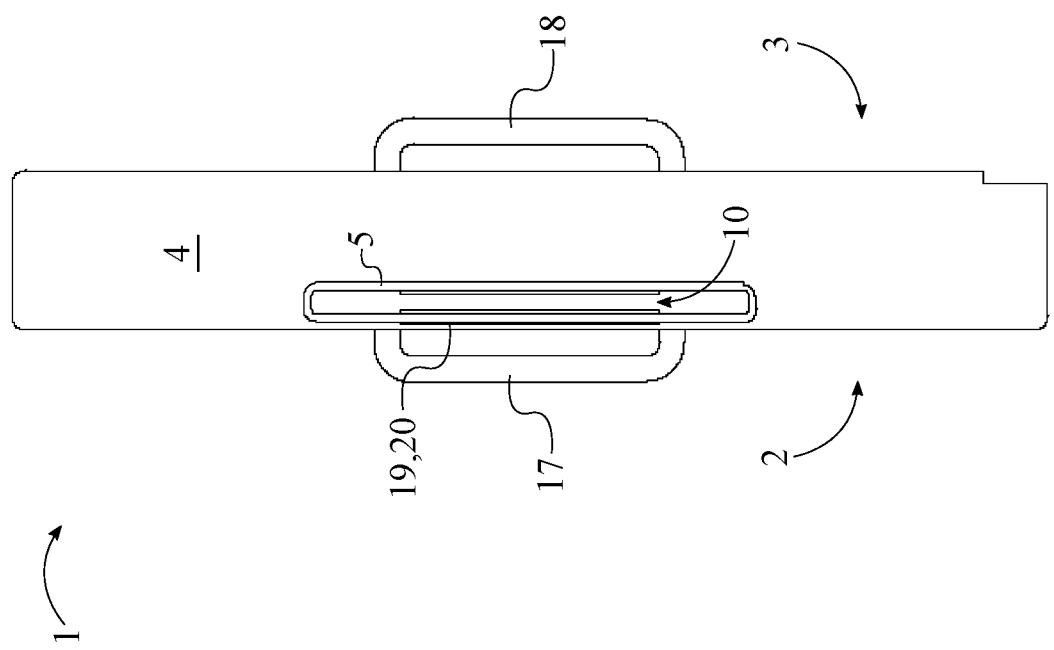
FIG. 4 is a right-side view of the present invention.
Figure 5:
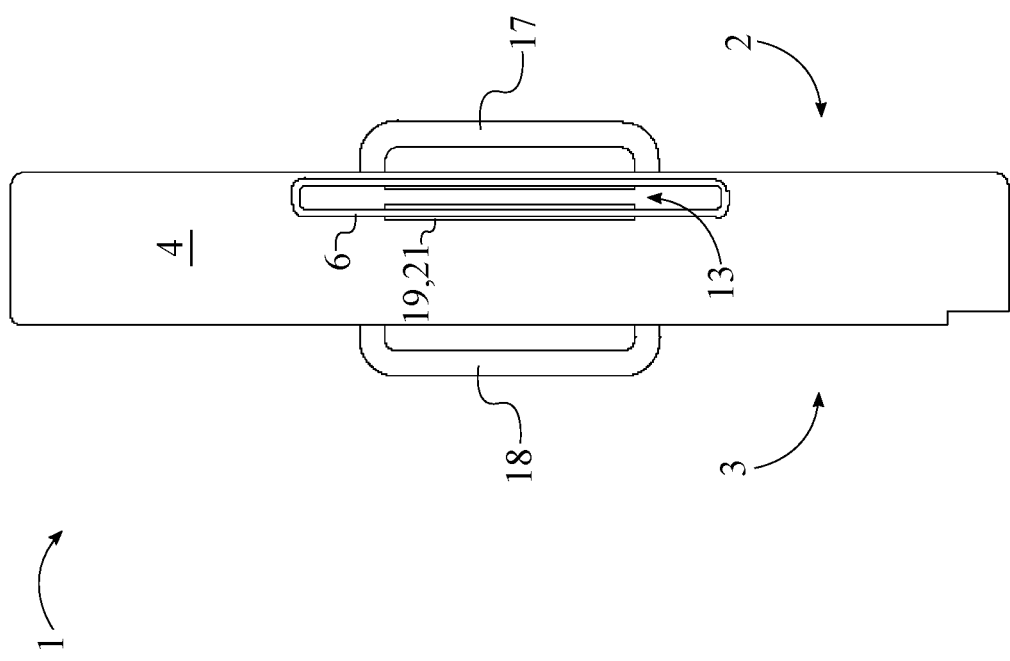
FIG. 5 is a left-side view of the present invention.

The general configuration of the aforementioned components allows the present invention to effectively cover body parts of the user. With reference to FIGS. 2 and 3, the pillowcase 1 comprises a first face 2, a second face 3, and a lateral portion 4. The first face 2, the second face 3, and the lateral portion 4 are parts of the pillowcase 1 which allow the first sash 5 and the second sash 6 to be properly positioned. The first sash 5 and the second sash 6 each comprise a fixed end 7 and a free end 8. The first sash 5 and the second sash 6 are externally positioned to the pillowcase 1. This properly positions the first sash 5 and the second sash 6 to the outer area of the pillowcase 1 rather than within the pillowcase 1. The fixed end 7 of the first sash 5 is connected adjacent to the lateral portion 4. Similarly, the fixed end 7 of the second sash 6 is connected adjacent to the lateral portion 4, opposite the fixed end 7 of the first sash 5. This arrangement allows the first sash 5 and the second sash 6 to cover different areas of body parts of the user. In more detail, the first sash 5 may be used to cover the left shoulder of the user, and the second sash 6 may be used to cover the right shoulder of the user. The fixed end 7 of the first sash 5 and the fixed end 7 of the second sash 6 are preferably sewn onto the lateral portion 4 of the pillowcase 1. The free end 8 of the first sash 5 and the free end 8 of the second sash 6 allow the user to freely position the first sash 5 and the second sash 6 on any body part of the user.

Figure 6:
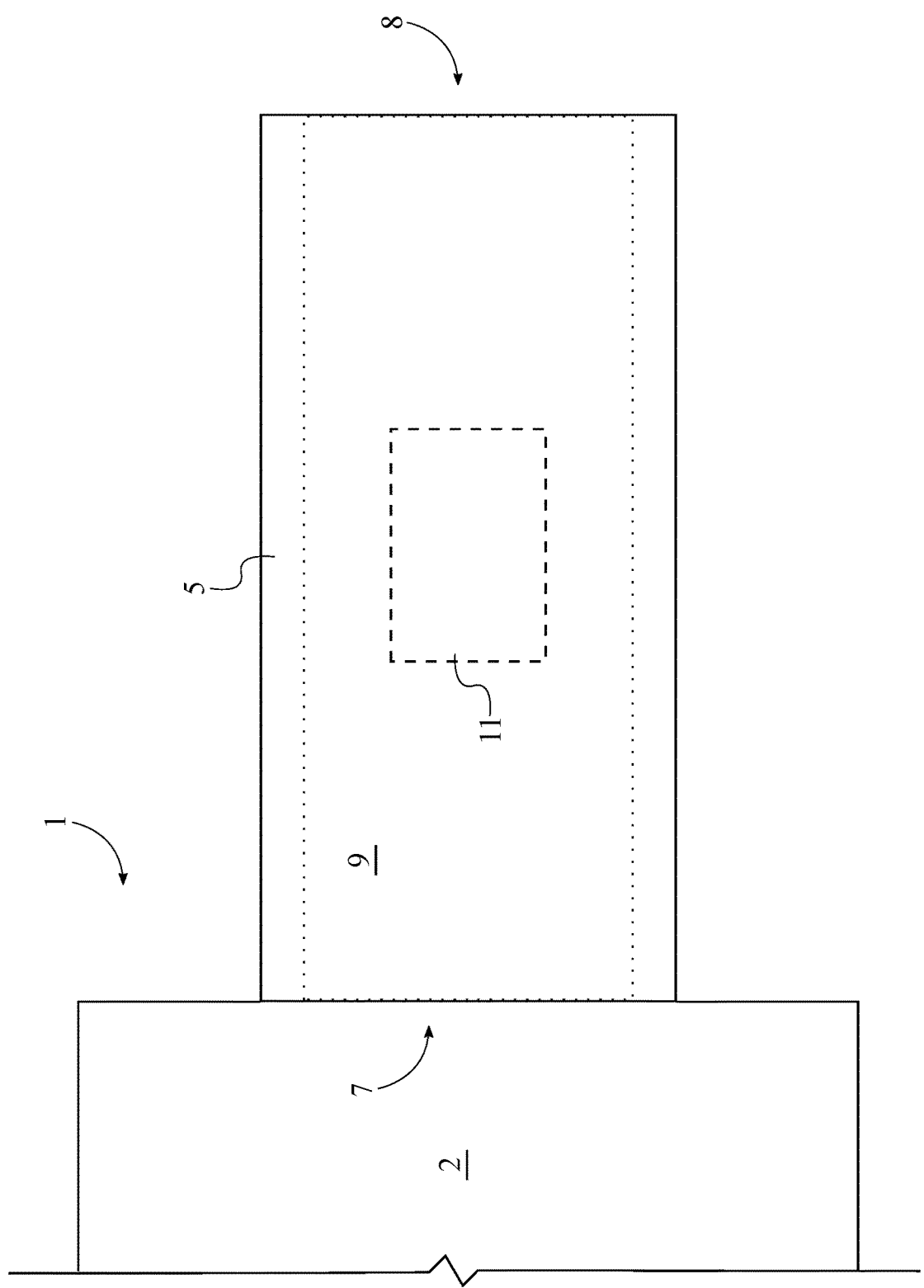
FIG. 6 is a schematic diagram of the present invention displaying the first pocket and the at least one first therapeutic pack.

With reference to FIG. 6, the present invention may further comprise a first pocket 9, which allows the first sash 5 to receive a therapeutic insert. The first pocket 9 is a recessed area within the first sash 5 that is able to receive a therapeutic insert. The first pocket 9 traverses from the free end 8 of the first sash 5 to the fixed end 7 of the first sash 5. The arrangement positions the first pocket 9 within the first sash 5 and provides enough area to receive one or more therapeutic inserts. In addition, the present invention may further comprise a first opening fastener 10. The first opening fastener 10 is operatively integrated into the free end 8 of the first sash 5, wherein the first opening fastener 10 is used to selectively allow access to the first pocket 9. The first opening fastener 10 may be any type of fastener such as, but not limited to, a hook-and-loop fastener, a draw-string, or a button fastener. Moreover, the present invention may further comprise at least one first therapeutic pack 11. The at least one first therapeutic pack 11 may be any type of therapeutic insert such as, but not limited to, a heating pack or a cooling pack. The at least one first therapeutic pack 11 is positioned within the first pocket 9. This arrangement allows the user to cover any body part with the first sash 5 and provides therapeutic support through the first sash 5 with the at least one first therapeutic pack 11.

Figure 7:
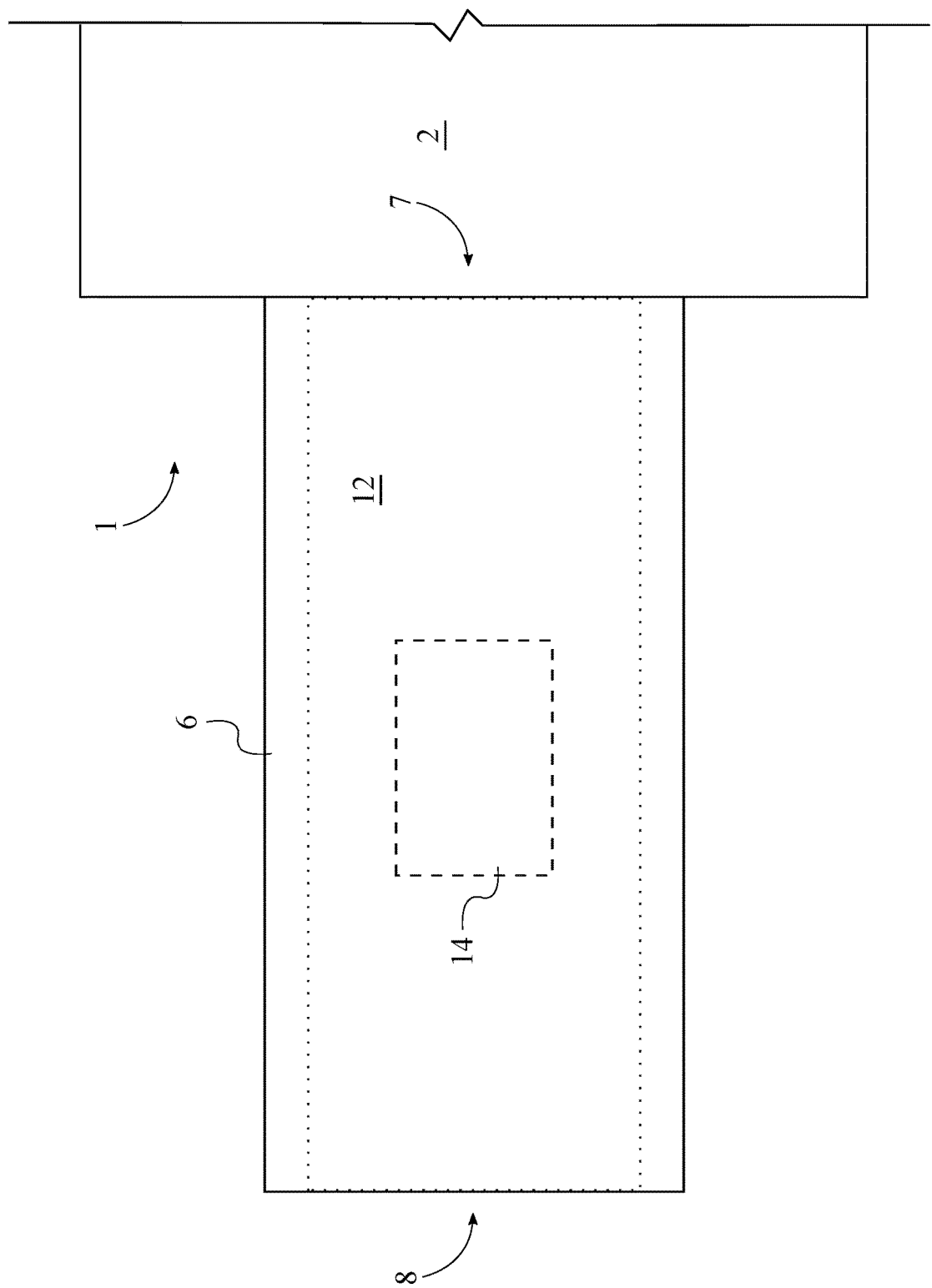
FIG. 7 is a schematic diagram of the present invention displaying the second pocket and the at least one second therapeutic pack.

Similarly, and with reference to FIG. 7, the present invention may further comprise a second pocket 12, which allows the second sash 6 to receive a therapeutic insert. The second pocket 12 is a recessed area within the second sash 6 that is able to receive a therapeutic insert. The second pocket 12 traverses from the free end 8 of the second sash 6 to the fixed end 7 of the second sash 6. The arrangement positions the second pocket 12 within the second sash 6 and provides enough area to receive one or more therapeutic inserts. In addition, the present invention may further comprise a second opening fastener 13. The second opening fastener 13 is operatively integrated into the free end 8 of the second sash 6, wherein the second opening fastener 13 is used to selectively allow access to the second pocket 12. The second opening fastener 13 may be any type of fastener such as, but not limited to, a hook-and-loop fastener, a drawstring, or a button fastener. Moreover, the present invention may further comprise at least one second therapeutic pack 14. The at least one second therapeutic pack 14 may be any type of therapeutic insert such as, but not limited to, a heating pack or a cooling pack. The at least one second therapeutic pack 14 is positioned within the second pocket 12. This arrangement allows the user to cover any body part with the second sash 6 and provide therapeutic support through the second sash 6 with the at least one second therapeutic pack 14.

Figure 8:
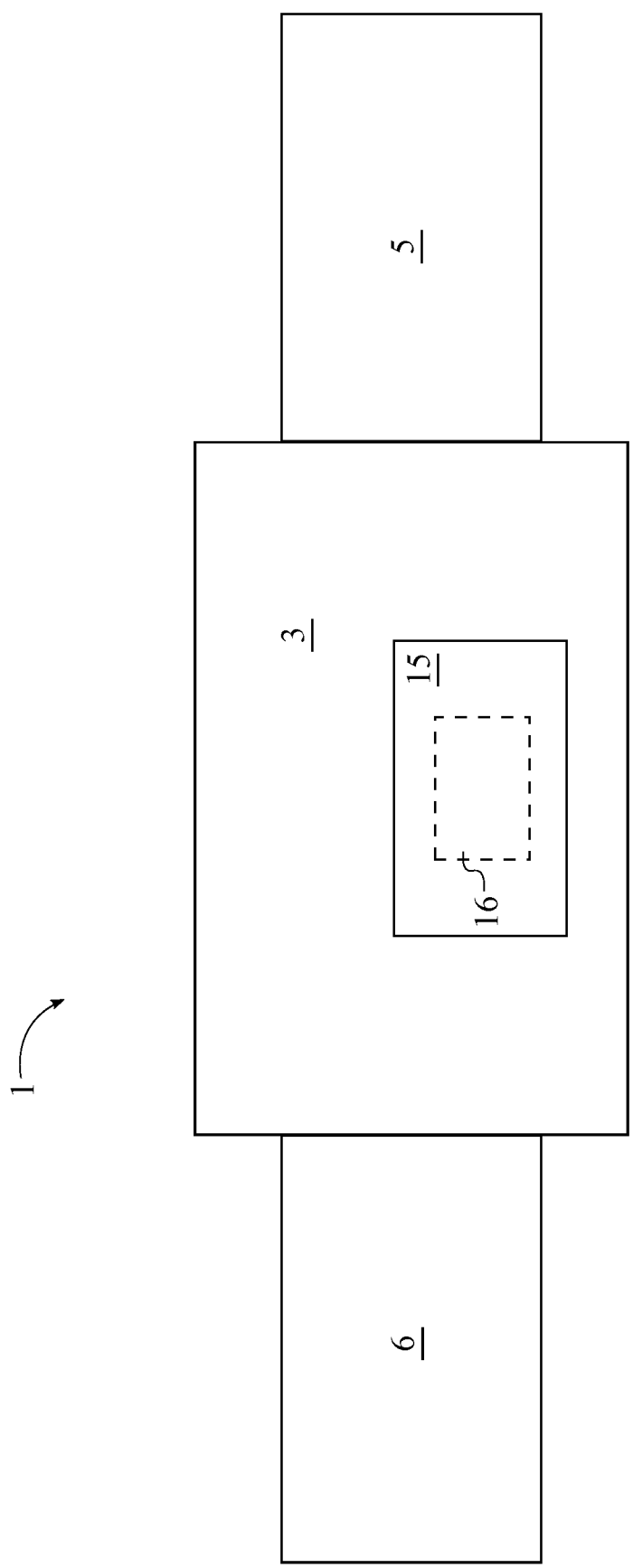
FIG. 8 is a schematic diagram of the present invention displaying the third pocket and the at least one third therapeutic pack.

With reference to FIG. 8, the present invention may further comprise a third pocket 15, which allows the pillowcase 1 to receive a therapeutic insert. The third pocket 15 is a recessed area of the pillowcase 1. The third pocket 15 is integrated into the second face 3 of the pillowcase 1. This arrangement properly positions the third pocket 15 to allow the user to distinguish the second face 3 from the first face 2. In addition, the present invention may further comprise at least one third therapeutic pack 16. The at least one third therapeutic pack 16 may be any type of therapeutic insert such as, but not limited to, a heating pack or a cooling pack. The at least one third therapeutic pack 16 is positioned within the third pocket 15. This arrangement allows the user to provide therapeutic support through the pillowcase 1 with the at least one third therapeutic pack 16. In more detail, this arrangement allows the user to specifically provides therapeutic support to the neck or back of the user when lying down on the present invention.

Figure 9:
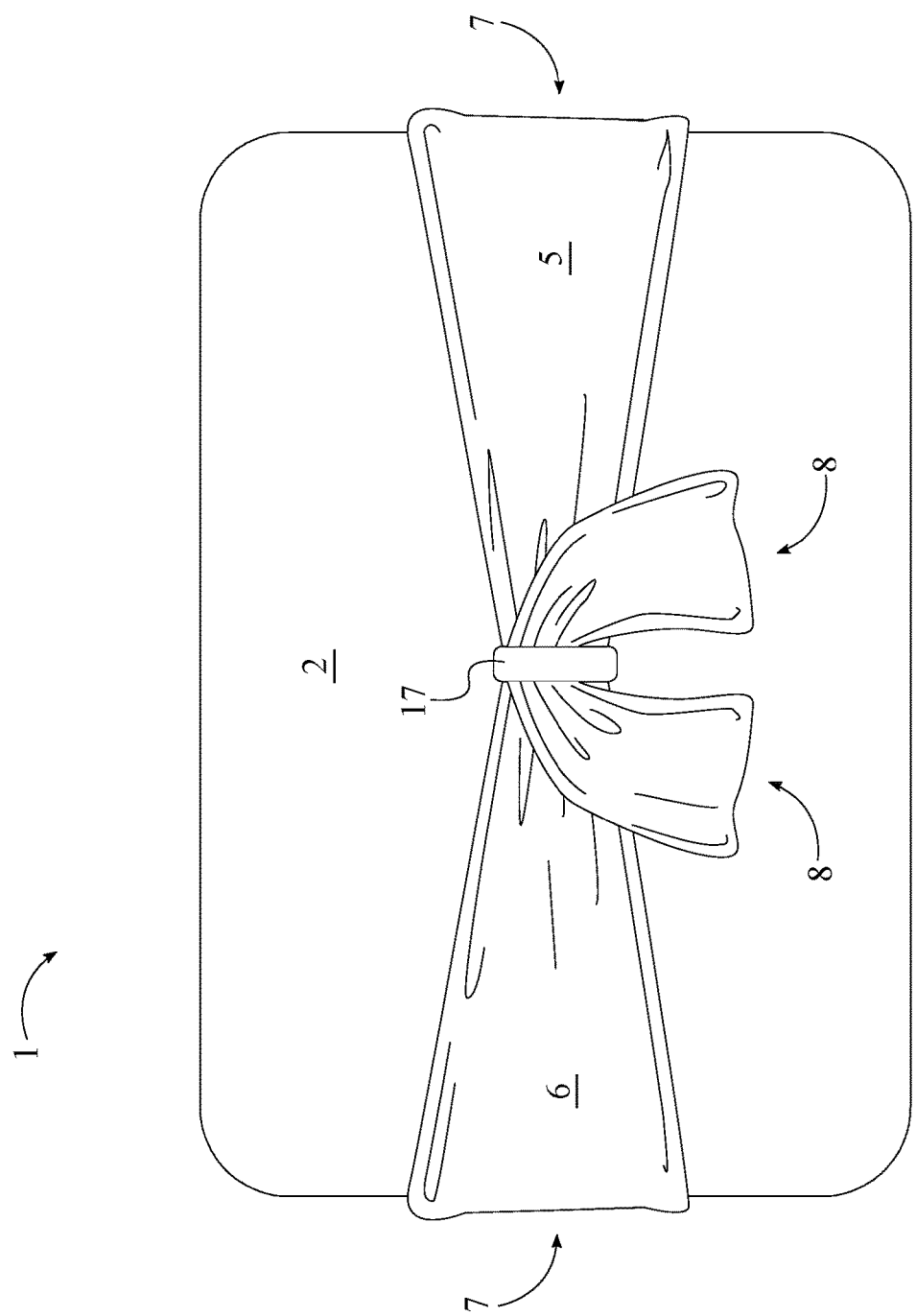
FIG. 9 is a front view of the present invention displaying the first bow loop, the first sash, and the second in a tied configuration.

With reference to FIG. 2, the present invention may further comprise a first bow loop 17, which allows the user to tie the first sash 5 and the second sash 6 in a bow shape when the present invention is not in use. The first bow loop 17 is centrally positioned and laterally connected onto the first face 2. This arrangement properly positions the first bow loop 17 to allow the user to distinguish the first face 2 from the second face 3. With reference to FIG. 9, the first bow loop 17, the first sash 5, and the second sash 6 can be in a tied configuration when the present invention is not in use and for a decorative purpose. The free end 8 of the first sash 5 and the free end 8 of the second sash 6 traverse through the first bow loop 17 in the tied configuration. This arrangement allows the first sash 5 and the second sash 6 to be secured in a bow shape on the first face 2.

Figure 10:
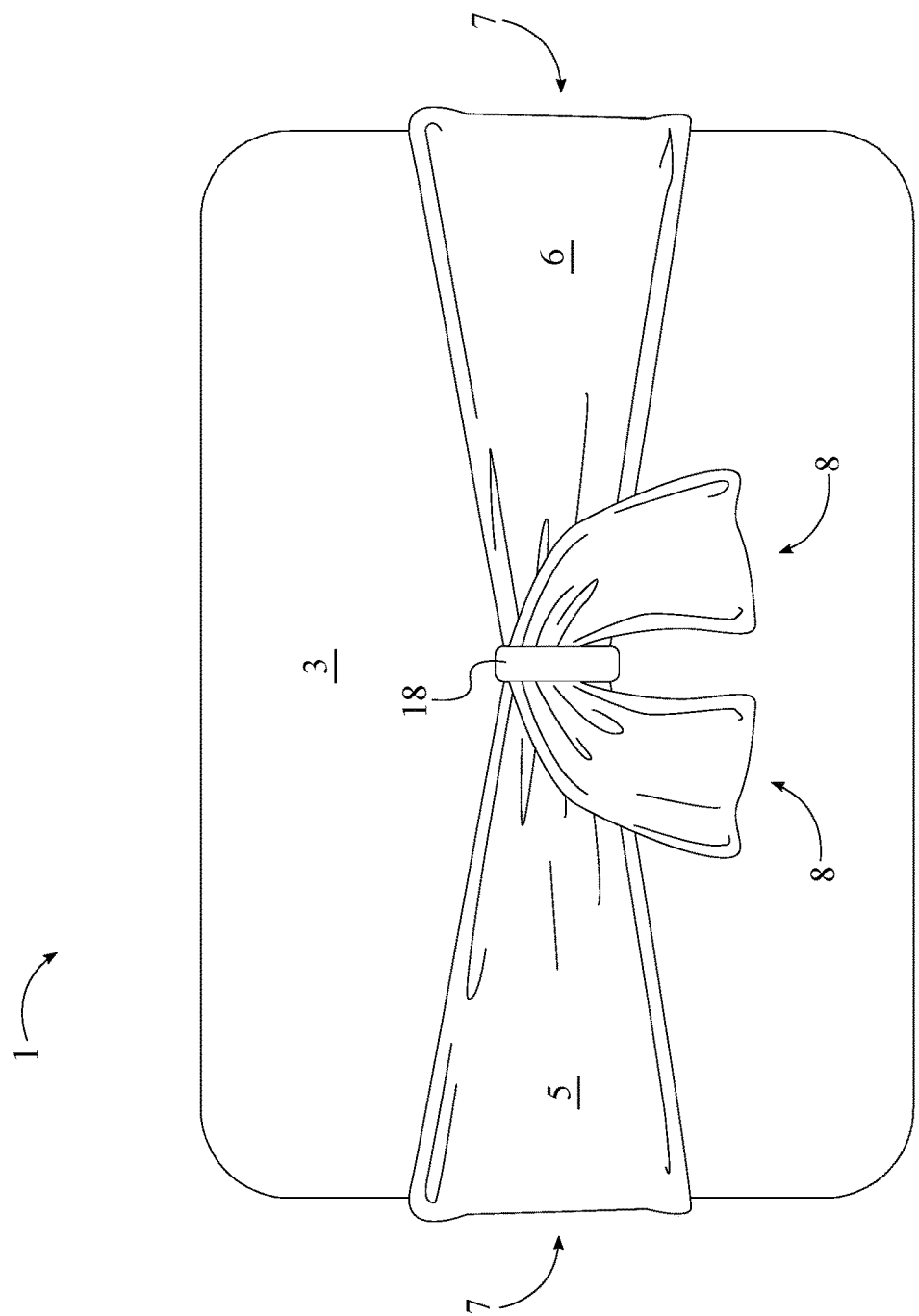
FIG. 10 is a rear view of the present invention displaying the second bow loop, the first sash, and the second in a tied configuration.

In order for the present invention to be aesthetically appealing on both its sides and with reference to FIG. 3, the present invention may further comprise a second bow loop 18 which allows the user to tie the first sash 5 and the second sash 6 in a bow shape when the present invention is not in use. The second bow loop 18 is centrally positioned and laterally connected onto the second face 3. This arrangement properly positions the second bow loop 18 to allow the user to interchangeably use the first face 2 or the second face 3 to display a bow shape with the first sash 5 and the second sash 6. With reference to FIG. 10, the second bow loop 18, the second sash 6, and the second sash 6 can be in a tied configuration when the present invention is not in use and for a decorative purpose. The free end 8 of the second sash 6 and the free end 8 of the second sash 6 traverse through the second bow loop 18 in the tied configuration. This arrangement allows the second sash 6 and the second sash 6 to be secured in a bow shape on the second face 3.

One of the purposes of the present invention is to block light by covering the eyes of the user with the first sash 5 and the second sash 6. This is effectively accomplished, wherein the first sash 5 and the second sash 6 are made of an opaque fabric material.

With reference to FIGS. 2 and 3, the present invention may further comprise a sash fastener 19 that allows the use to fasten the first sash 5 and the second sash 6 together when using the present invention. The sash fastener 19 may be any type of fastener such as, but not limited to, a button fastener or hook-and-loop fastener. The sash fastener 19 comprises a first interlocking portion 20 and a second interlocking portion 21. The first interlocking portion 20 is connected adjacent to the free end 8 of the first sash 5. Similarly, the second interlocking portion 21 is connected adjacent to the free end 8 of the second sash 6. This arrangement properly positions the sash fastener 19, wherein the user can easily fasten the first sash 5 to the second sash 6 and the user is not burdened by the sash fastener 19 when using the present invention.

In another embodiment of the present invention, the pillowcase 1 may include a pillowcase fastener that prevents any pillow from falling out of the pillowcase 1. The pillowcase fastener may be positioned wherever the pillow-receiving opening is positioned depending on the type of pillow enclosure of the pillowcase 1. The pillowcase fastener may be any type of fastener such as, but not limited to, a zipper fastener or button fastener. In addition, the first sash 5 and the second sash 6 each may include a pacifier. The pacifier may be a fur piece, a pom-pom piece, or other similar piece that can aid the user to fall asleep. The pacifier may be connected adjacent to the free end 8.

Although the invention has been explained in relation to its preferred embodiment, it is to be understood that many other possible modifications and variations can be made without departing from the spirit and scope of the invention as hereinafter claimed.

What is claimed is:
1. A therapeutic pillow sham comprises:
   a pillowcase;
   a first sash;
   a second sash;
   the pillowcase comprising a first face, a second face and a lateral portion;
   the first face and the second face being oppositely located to each other;

the lateral portion being perimetrically connected in between the first face and the second face;

the first sash and the second sash each comprising a fixed end and a free end;

the first sash and the second sash being externally positioned to the pillowcase;

the fixed end of the first sash being connected to the lateral portion;

the fixed end of the second sash being connected to the lateral portion, opposite the fixed end of the first sash;

a first bow loop;

the first bow loop being centrally positioned onto the first face;

the first bow loop being laterally connected onto the first face;

a second bow loop;

the second bow loop being centrally positioned onto the second face;

the second bow loop being laterally connected onto the second face;

the first bow loop, the first sash and the second sash being configured to be in a first tied configuration;

in response to the first bow loop, the first sash and the second sash being in the first tied configuration, the free end of the first sash and the free end of the second sash jointly traversing through the first bow loop;

the second bow loop, the first sash and the second sash being configured to be in a second tied configuration; and in response to the second bow loop, the first sash and the second sash being configured to be in the second tied configuration, the free end of the first sash and the free end of the second sash jointly traversing through the second bow loop.

2. The therapeutic pillow sham as claimed in claim 1 comprises:

a first pocket; and the first pocket traversing from the free end of the first sash to the fixed end of the first sash.

3. The therapeutic pillow sham as claimed in claim 2 comprises:

a first opening fastener; and the first opening fastener being operatively integrated into the free end of the first sash, wherein the first opening fastener is used to selectively allow access to the first pocket.

4. The therapeutic pillow sham as claimed in claim 2 comprises:

at least one first therapeutic pack; and the at least one first therapeutic pack being positioned within the first pocket.

5. The therapeutic pillow sham as claimed in claim 1 comprises:

a second pocket; and the second pocket traversing from the free end of the second sash to the fixed end of the second sash.

6. The therapeutic pillow sham as claimed in claim 5 comprises:

a second opening fastener; and the second opening fastener being operatively integrated into the free end of the second sash, wherein the second opening fastener is used to selectively allow access to the second pocket.

7. The therapeutic pillow sham as claimed in claim 5 comprises:

at least one second therapeutic pack; and the at least one second therapeutic pack being positioned within the second pocket.

8. The therapeutic pillow sham as claimed in claim 1 comprises:

a third pocket; and the third pocket being integrated into the second face.

9. The therapeutic pillow sham as claimed in claim 8 comprises:

at least one third therapeutic pack; and the at least one third therapeutic pack being positioned within the third pocket.

10. The therapeutic pillow sham as claimed in claim 1, wherein the first sash and the second sash are made of an opaque fabric material.

11. The therapeutic pillow sham as claimed in claim 1 comprises:

a sash fastener;

the sash fastener comprises a first interlocking portion and a second interlocking portion;

the first interlocking portion being connected adjacent to the free end of the first sash; and the second interlocking portion being connected adjacent to the free end of the second sash.

* * * * *